United States Patent [19]

Bolton et al.

[11] Patent Number: 4,971,783

[45] Date of Patent: Nov. 20, 1990

[54] TISSUE PROCESSING FOR IMMUNOFLUORESCENCE MICROSCOPY

[75] Inventors: W. Kline Bolton; Robert M. Mesnard, both of Charlottesville, Va.

[73] Assignee: The University of VA Alumni Patents Foundation, Charlottesville, Va.

[21] Appl. No.: 443,838

[22] Filed: Nov. 22, 1982

[51] Int. Cl.$^5$ .................. G01N 1/00; G01N 1/30; A01N 1/00
[52] U.S. Cl. .................................. 424/3; 435/1
[58] Field of Search ............. 424/3, 75; 252/380; 27/22 R, 22 A

[56] References Cited

U.S. PATENT DOCUMENTS

| 2,393,580 | 1/1946 | Weiskopf | 424/3 |
| 3,961,097 | 6/1976 | Gravlee, Jr. | 424/3 |

OTHER PUBLICATIONS

Holt, S. J. et al. *J. Biophys. Biochem. Cytol* vol. 7, 1960 p. 383–386.
Holt, S. J. et al. J. Biophys. Biochem. Cytol. vol. 11, 1961 p. 31–45.
Humason, G. L., *Animal tissue Techniques*, W. H. Freeman & Co., San Francisco 1972, p. 35,419.
Culling, C. F. A., *Handbook of Histopathological and Histochemical Techniques*, Butterworths, London, 1974, p. 46,629.

*Primary Examiner*—Johnnie R. Brown
*Assistant Examiner*—Jeremy M. Jay
*Attorney, Agent, or Firm*—John J. Byrne; Bradford E. Kile

[57] ABSTRACT

A tissue holding and processing technique suitable for immunofluorescence, histochemical, and light microscopic analysis of the same specimen. The tissue is first placed in formol sucrose, and then transferred to gum sucrose. The tissue is subsequently washed in phosphate buffered saline, then acetone-water, then acetone, and finally in xylene. Finally, the tissue is embedded in paraffin. Tissue processed according to the present invention may be stored indefinitely in the gum sucrose or paraffin.

18 Claims, 4 Drawing Sheets

FIG. 1a
FIG. 1b
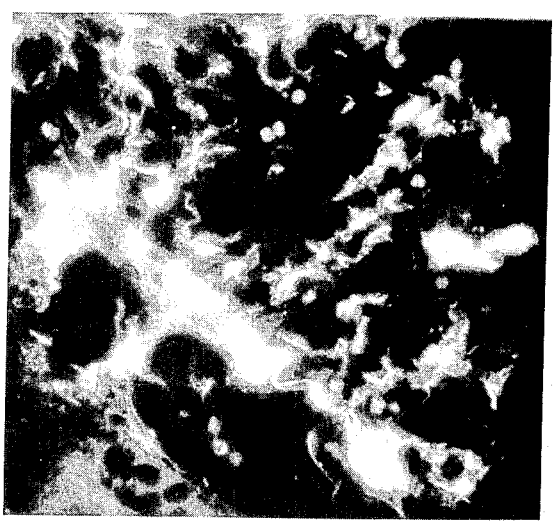
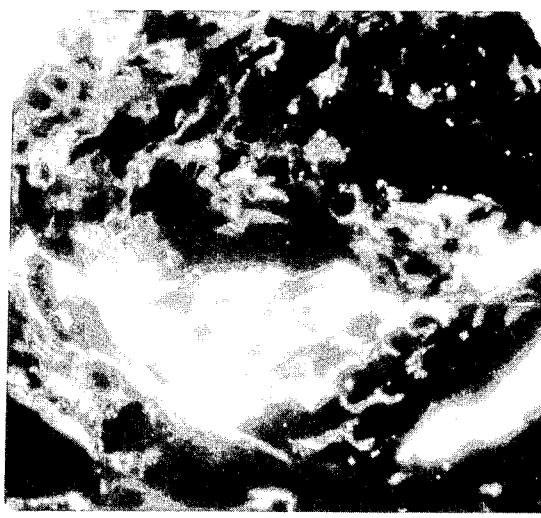
FIG. 1c
FIG. 1d

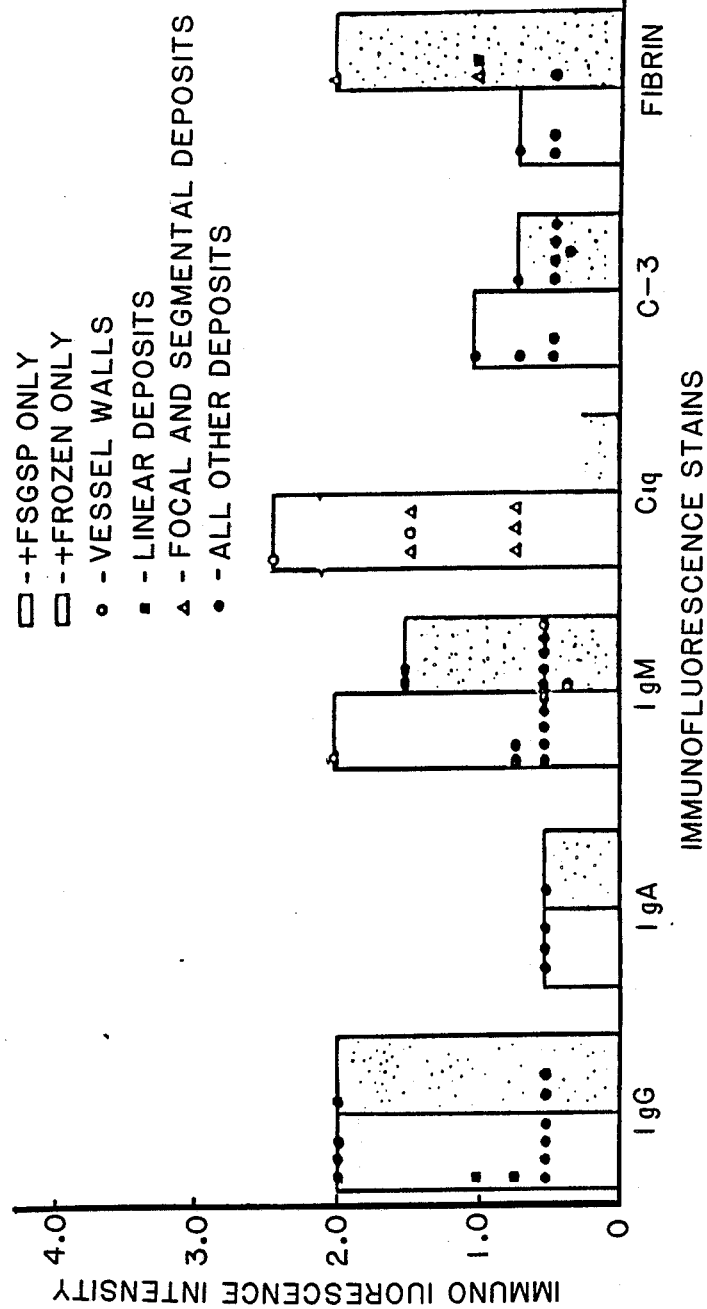

TISSUE PROCESSING FOR IMMUNOFLUORESCENCE MICROSCOPY

FIELD OF THE INVENTION

The present invention relates to a method of tissue processing for immunofluorescence. In addition, tissue processed according to the present method may be used for light and histochemical microscopy.

BACKGROUND OF THE INVENTION

The combination of electron and immunofluorescence with light microscopy evaluation of kidney biopsies has added much to knowledge about pathogenesis prognosis, and therapy of renal diseases. The imminent clinical use of immunoelectron microscopy, histochemical analysis, and in vitro culture of renal biopsies promises to add yet additional potential to the ability to better understood and treat renal diseases. However, the increased sophistication provided by these techniques also requires additional tissues. Furthermore, the inherent fragility of present immunofluoresent methods of tissue preservation requires improved methodology.

Many methods have been attempted to allow tissue preparation compatible for a variety of different histologic procedures, especially for light and immunofluorescent studies. Most of the prior methods have suffered from excessive laborious preparation, loss of tissue detail, loss of tissue antigens, or other problems. Conventional tissue preparation techniques are disclosed, for example, in U.S. Pat. No. 2,393,580 to E.C. Weiskopf.

SUMMARY OF THE INVENTION

The present invention provides a method of holding and processing tissue that allows the tissue to be fixed and transported by conventional means, paraffin embedded, and used for immunofluorescent microscopy. The method of the present invention produces results equal or superior to snap freezing for immunofluorescence. In addition, the method of the present invention permits the same paraffinembedded tissue to be used for light and histochemical microscopy.

Tissue processed by the method of the present invention is first placed in formol sucrose. After approximately 24 hours, the specimen is transferred to gum sucrose. After about 24 hours in gum sucrose, the tissue is washed in phosphate-buffered saline for two hours, transferred to acetone-water for a half-hour, then to three changes of pure acetone for one-half hour each. The tissue may then be washed with saline and embedded in paraffin. The tissue processed by the method of the present invention may be stored indefinitely in the gum sucrose or paraffin.

It is an advantage of the present invention that tissue processed according to the invention may be transported with regular ice rather than dry ice, and stored in a standard refrigerator.

Anther advantage of the present invention is that tissue processed according to the invention does not require flammable storage media.

It a feature of the present invention that tissue prepared according to the invention may be examined at a higher power than frozen sections with good morphology and with lack of the diffusion artifact often observed at high power with frozen tissue at fluorescent stains.

It is another feature of the present invention that tissue prepared according to the invention may be maintained in formol sucrose in the cold for months or years.

It is an object of the present invention to provide a method for convenient, space-conserving storage and retrieval, preservation of tissues for years without loss of antigenicity lack of dependence on freezer space and electrical power, and utilization of processed tissue for routine light and histochemical analysis.

BRIEF DESCRIPTION OF THE DRAWINGS

FIG. 1 comprises illustrative photographs of glomeruli from patients with:
  a membranous nephropathy and epimembranous deposits by electron microscopy;
  b: focal nephritis and hematuria;
  c: membranoproliferative glomerulonephitis;
  d: extracapillary glomerulonephitis.

FIG. 3 comprises a Scattergram of the individual stains and patterns for all specimens negative by one method but positive by the other. Seventy-nine percent differ in intensity from zero by 1.0 or less, with approximately equal distribution between the two methods.

DETAILED DESCRIPTION

Figure 2A:
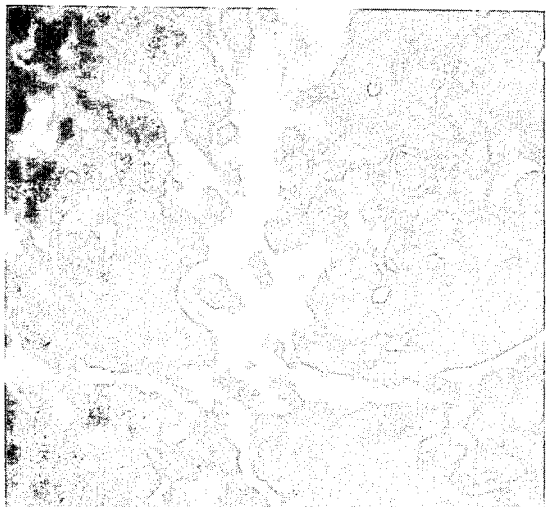
FIG. 2 comprises photographs demonstrating findings in patients with:
  a: focal glomerulosclerosis;
  b: acute crescentic glomerulonephritis secondary to anti-GBM antibody;
  c: exudative proliferative glomerulonephritis by light microscopy, and subendothelial ultrastructural deposits without humps; and
  d: artifactual non-specific staining for serum proteins in a "stasis" pattern.

Immunofluorescence examination of renal biopsies is an essential part of the diagnostic schema for many kidney diseases. Two decades ago, light microscopy alone would have sufficed to study kidney biopsies—now, fluorescence and electron microscopy are expected. In the near future, immunoelectron microscopy and histochemical analysis may also be a required part of kidney biopsy interpretation. There are several major problems with this proliferation of capability. First, more pieces of tissue are required, and different fixatives are needed. Second, many of these techniques are not available locally and nephrologists must refer kidney biopsies to centers for evaluation. Experience with these two problems led to the development of the invention described in this specification. The present invention provides a holding and processing method which allows tissue to be fixed and transported by conventional methods, paraffin embedded, and used for immunofluorescence microscopy. The results are equal or superior to snap freezing methods for immunofluorescence. In addition, the same paraffin embedded tissue may be used for light and histochemical microscopy. The method of the present invention may be understood by reference to the following examples, which illustrate the invention but are not intended to limit the scope of the invention.

EXAMPLES

At the time of renal biopsy, tissue was divided into portions. One portion was placed on a piece of cork and snap-frozen in dry-ice isopentane and another portion was placed in 0°-4° C formol sucrose selection This solution can be preparated by combining 2 gm. of NaH$_2$PO$_4$.H$_2$O, 3.25 gm of Na$_2$HPO$_4$, 37.5 gm sucrose, 50 ml formaldehyde, 0.05 gm NaN$_3$ and 450 ml deionized water. After 22-24 hours the specimen was transferred to gum sucrose, 0°-4° C. The latter was prepared by combining 150 gm sucrose, 5 g:n gum Acacia, 0.05 gm NaN$_3$, mixing dry and adding deionized water 500 ml.

In order to determine the optimal times of immersion of tissue in formol sucrose and gum sucrose, a rabbit was injected with sheep nephrotoxic serum to produce nephrotoxic serum nephritis. Tissue was obtained at sacrifice and blocks placed in formol sucrose for different times and gum sucrose in the second step for variable times. Tissue was then processed as described below and stained with fluorescein labeled anti-sheep IgG antiserum. Afer 18-24 hours in gum sucrose, tissue was washed in phosphate buffered saline, pH 7.3 (hereinafter PBS) for 2 hr., transferred to 50% acetone-water at 0°-4° C. for 30 min., then to 3 changes of 100% acetone for 30 min. each at 0°-4° C. This was followed by three 15 min. changes of xylene and embedding via three changes of paraffin, 58°-61° C., 15 min. each. Tissue may be stored indefinitely in the gum sucrose or paraffin.

Tissue sections 3 microns thick were air dried at 60° C. for 1 hr., then deparaffinized through 3 changes of xylene 5 min. each and ethanol, 100%, 95%, and 80% for 5 min. each. They were then washed twice for 5 min. in phosphate buffered saline. It was important to float the tissue sections on water which contained no additives. Three sections were placed on each slide. After blotting phosphate buffered saline from around sections, a drop of 0.1% pronase in phosphate buffered saline (protease, Sigma Type VII) was placed on the sections. Various concentrations and lengths of digestion were examined with trypsin during the preliminary studies with pronase. Slides were incubated at 37° C. in a wet box for 15 min. After two 5 min. washes in PBS, sections were processed for immunofluorescence using monospecific fluorescein labeled antibody with incubation in a wet box at 37° C. for 1 hr., followed by 2 washes in PBS, 5 min. each, and coverslipping with Gelvatol (sold by Monsanto, Inc., St. Louis, Mo.). At all times the sections and slides were handled very gently to minimize dislodgement of tissue. Sections were examined with antisera to human IgG, IgA, IgM, Clq, C-3, Tamm-Horsfall protein, fibrinogen, alpha-2-macroglobulin, and kappa and lambda light chain. It was essential to use affinity isolated, mouse liver powder absorbed anti-human IgG for good results with that stain. All fluorescein labeled antisera were examined against a battery of known positive and negative tissues to ascertain their reactivity and monospecificity. Tissue sections were examined with a Zeiss research fluorescence microscope with a primary filter at 490 nm and a secondary filter of 515 nm. The excitation source was a 50 watt D.C. HBO lamp. Fluorescence was graded on an eleven point scale with negative equal to zero; 0-tr, 0.25; tr, 0.50; tr-1+, 0.75; 1+, 1.0; 1-2+, 1.5; 2., 2.0; 2-3+, 2.5; 3+, 3.0; 3-4+, 3.5; and 4+, 4.0.

Data were entered into a computer using the 11 point grading system. Findings were considered in the categories of granular glomerular basement membrane (hereinafter GBM), linear CBM, mesangial, granular or linear tubular basement membrane (hereinafter TBM), and vessel wall deposits. Only samples containing adequate glomeruli for both the frozen and formol sucrose, gum sucrose, paraffin (hereinafter "FSGSP") methods were considered in the analysis. For quantitative comparative analysis, results with IgG, IgM, C-3, Clq, IgA, and fibrinogen were examined. Frozen section results were considered the "standard". For intensity comparison, each pattern and staining section of FSGSP was assigned a value of zero if FSGSP staining was of the same intensity as frozen, negative if less, and positive if of greater intensity than frozen. The range of FSGSP could be from −4 to 4+After entering the data, all manipulations were performed via the computer.

Staining of deparaffinized sections for non-specific esterase activity was performed by the method of Mueller et al., 5 Eur. J. Immunol. 274 (1975) and Barka et al., 10 J. Histochem. Cytochem. 741 (1962). After 3 washes in deionized water and 30 min. air drying, sections were incubated for 45 min. in pararosanilin/alpha-naphthyl acetate/sodium nitrite pH 6.0, mixed immediately prior to incubation. Sections were washed with water, counter stained with 1% methyl green, washed, dried and mounted. Non-specific esterase activity was indicated by dark red cytoplasmic granules. Sections 3-microns thick were cut and stained by routine methods with hematoxylin-eosin (HSE) and periodic acid-Schiffs reagent (PAS).

Fifty biopsies contained glomeruli in both the frozen specimens and FSGSP, and were adequate for diagnosis by light and electron microscropy. The histologic diagnoses are listed in Table 1. A wide spectrum of disease entities is represented, including immunologically and non-immunologically mediated processes. The five normal biopsies were obtained at the time of transplantation. Representative photographs of the immunofluorescence findings are presented in FIGS. 1 and 2. Distinct deposits in the mesangium, granular GBM, linear GBM, and crescents are illustrated. Very low background fluorescence with excellent resolution is present in all sections. An endocapillary stasis pattern from fixation of proteins in capillary lumina (FIG. 2d) was occasionally observed, but was easily distinguishable from specific deposits.

TABLE 1

| Histologic Diagnoses | |
|---|---|
| Diagnosis | Number |
| Transplant rejection | 9 |
| Crescentic nephritis, idiopathic | 5 |
| Proliferative nephritis | 5 |
| Systematic lupus erythematosus | 5 |
| Normal | 5 |
| Focal glomerular sclerosis | 4 |
| End stage | 3 |
| Hypertension | 3 |
| Interstitial nephritis | 3 |
| Atheromatous emboli | 2 |
| Diabetes | 2 |
| Membranous nephropathy | 2 |
| Scleroderma | 1 |
| Familial nephritis | 1 |
| TOTAL | 50 |

Figure 2B:
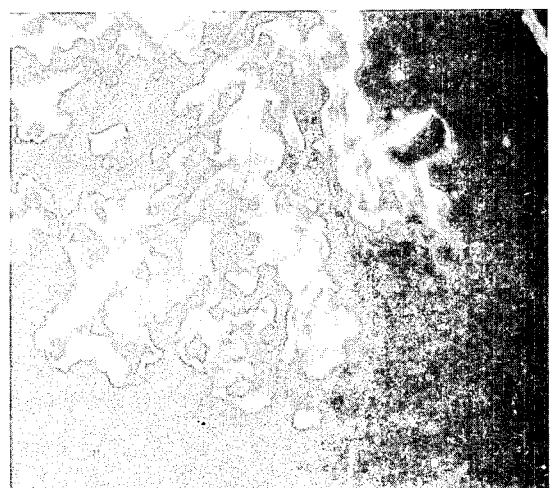
Figure 2C:
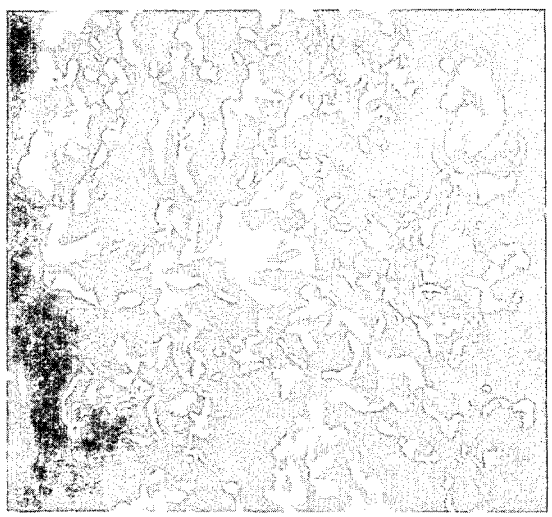
Figure 2D:
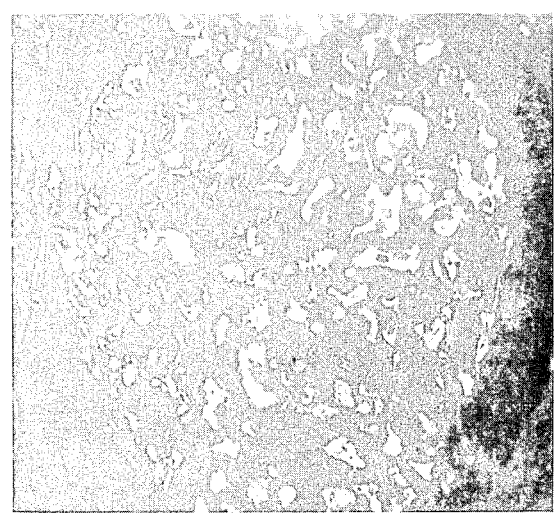

The comparison of staining between frozen and FSGSP is given in Table 2. The third column, "non-significant", represents those sections which were negative by one method and 0-trace positive by the other. These differences were considered of little significance and so are included in the agreement column. Thus, agreement for the 6 stains examined in detail ranged from 86 to 98%. The biopsies considered to be accurately positive by FSGSP but negative by frozen in an intensity greater than trace are given in the next column, followed by those sections considered to be false positive by FSGSP. These latter two assessments were based on the pattern of distribution of the stain, clinical data, and findings by light and electron microscopy. The last column provides an accounting of sections positive by frozen only with intensity greater than trace. Inclusion of the additional positives detected by FSGSP provides the total accuracy of the method, which ranged from 94 to 100%. Eight of 9 crescents were detected by FSGSP. FIG. 3 illustrates the scores of individual biopsies and stains when a specimen was negative by one method and positive by the other. The majority of negative staining discrepancies were of trace amount (73%) with 88% of biopsies differing by a quantity of 1.5 or less and only 12% by a quantity of 2.0 or greater for the 6 stains combined. Of note is the close correlation of C-3 (Table 2, FIG. 3) with essentially all of the differences between the two methods being of trace to 1+intensity. C-3 was also clearly detected when present as linear CBM deposits (FIG. 2b). In all cases, only direct staining was performed. As can be observed from both Table 2 and FIG. 3. FSGSP detected slightly more deposits than the frozen method.

though the deposits were still focal and segmental. Nonetheless, all other discontinuous C-3 deposits were distinctly granular (FIG. 2a) and linear deposits distinctly linear (FIG. 2b). This finding on FSGSP of linear TBM C-3 deposits was as consistent as the granular GBM deposits of C-3 on frozen section. The results with the other stains were evaluated non-quantitatively. IgE was present in several patients as linear GBM deposits by both frozen and FSGSP, as well as granular deposits by both methods. In each case, there was good agreement and no differences sufficient to influence the tendered diagnosis.

There were several obvious and attractive differences between FSGSP and frozen processing in both the quantitative and subjective results. (1) Several internal positive controls for tissue antigenicity were present in the FSGSP sections. Protein droplets were vividly apparent with numerous stains in patients by FSGSP, especially those with proteinuria. Casts stained more vividly with FSGSP, including Tamm-Horsfall protein in casts and tubular cells. (2) The presence of alpha-2-macroglobulin in an endocapillary pattern provided a good control for glomerular stasis. (3) The resolution at 100 × with 8 × eyepieces was superior with FSGSP (FIG. 2B) and allowed assessment of deposits more easily than with frozen. (4) FSGSP processed tissue retained antigenicity for long periods of time. Sections stored in paraffin for 2-3 years have been restained and no differences were observed. (5) Formol surcrose/gum sucrose appears to be an excellent storage/transporting medium. Embedded tissue stored for up to 7 months in

TABLE 2

Comparison of Immunofluorescence Staining, FSGSP and Frozen

| Stain | (+) FSGSP & Frozen | (−) FSGSP & Frozen | NS* FSGSP/ Frozen | Agreement | True (+) FSGSP (−) Frozen | False (+) FSGSP (−) Frozen | Total FSGSP Accuracy | (+) Frozen Only |
|---|---|---|---|---|---|---|---|---|
| IgG | 28% | 48% | 12% | 88% | 6% | 4% | 94% | 2% |
| IgA | 4 | 86 | 8 | 98 | 0 | 0 | 98 | 0 |
| IgM | 44 | 24 | 22 | 90 | 6 | 0 | 96 | 4 |
| C1q | 28 | 58 | 0 | 86 | 14 | 0 | 100 | 0 |
| C-3 | 38 | 42 | 14 | 94 | 4 | 0 | 98 | 2 |
| Fibrin | 14 | 72 | 6 | 92 | 2 | 0 | 94 | 6 |
| Crescents (9) | 6/9 | | 2/9 | | | | 8/9 | 1/9 |

*NS = trace deposits vs negative, one method compared to the other

Figure 4:
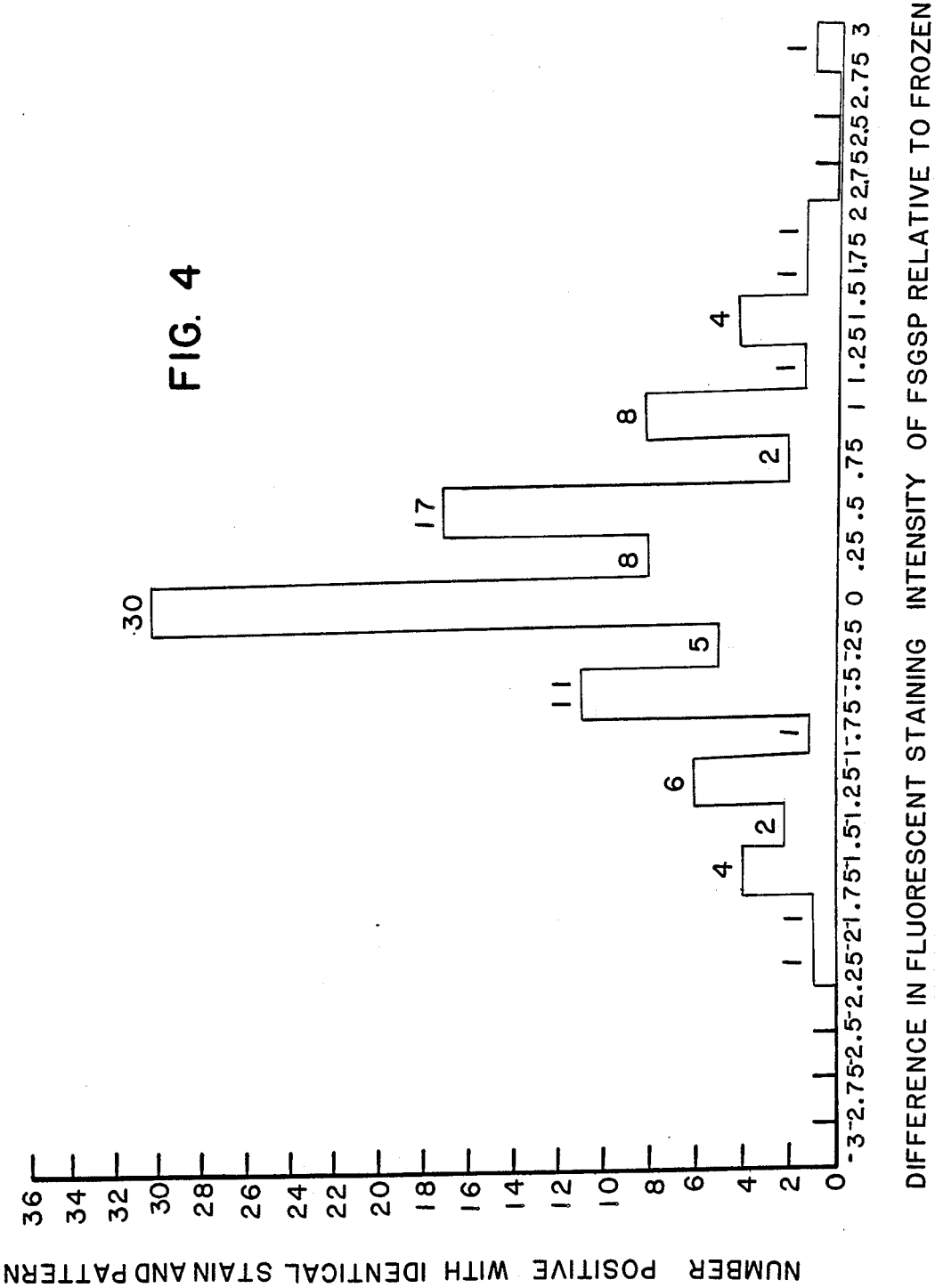
FIG. 4 illustrates differences in intensity of staining between the method of the invention and frozen sections. All stains and all patterns positive by both methods comprise the evaluated group. There is 85% agreement between the two for intensity of +1.0, regardless of whether deposits were in vessels, tubules or glomeruli.
Figure 4:
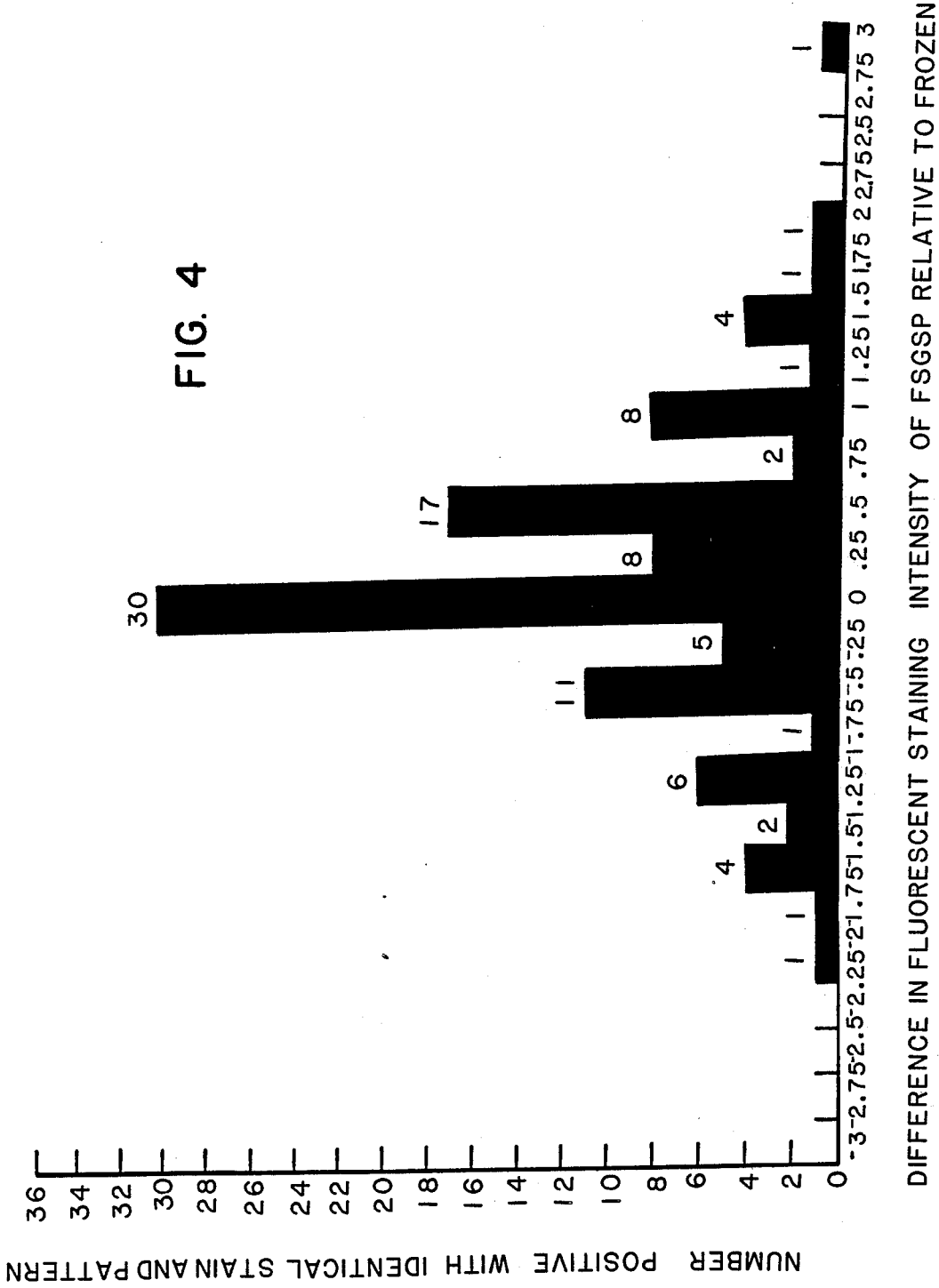

Analysis of the two techniques is provided using a different approach in FIG. 4. All sections which were positive by both the FSGSP and frozen methods, in the identical staining pattern (i.e., granular mesangial, linear GBM, granular vessel wall) were compared relative to staining intensity. Identical intensity equals zero. If FSGSP was stronger, the score is positive, if less than frozen, a negative score. Eighty-five percent of FSGSP positive scores were within 1.0 of the frozen, with only 7.7% with a lower intensity relative to frozen of more than 1.0. Indeed, slightly more intensity was present by FSGSP relative to frozen (43 vs. 31) when staining was not of identical intensity.

The pattern of deposition in the kidney biopsies was generally the same with FSGSP and frozen. Granular deposits appeared more distinct and well delineated by FSGSP than with frozen, but in the same pattern. This was true for GBM, mesangial and vascular deposits. The only discrepancy observed was in the TBM staining for C-3. Focal and segmental granular C-3 deposits were observed along the TBM in various nephropathies and in normals. This pattern assumed a more nearly linear or pseudolinear distribution with FSGSP, algum sucrose at 0° 4° C. and has shown identical staining patterns and intensity compared to the original portion of the tissue processed at the time of biopsy.

Additional details of these examples may be found in our publication "New Technique of Kidney Tissue Processing for Immunofluoresence Microscopy:Formol Sucrose/Gum Sucrose/Paraffin", published in *Laboratory Investigation* Volume 47, pages 206-213 (1982), which is incorporated herein by reference. It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A process for preparing and preserving tissue for pathological evaluation, comprising in sequence:
   providing tissue,
   immersing said tissue in a formol sucrose solution at a temperature between about 0° C. to 4° C. for a period of about 18 to 24 hours,
   immersing said tissue in a gum sucrose solution at a temperature between about 0° to 4° C. for a period of about 18 to 24 hours,
   washing said tissue in a phosphate-buffered saline solution,
   washing said tissue in an acetone-water solution,
   washing said tissue in acetone, and washing said tissue in xylene,
   to obtain processed tissue which after storage for up to seven months in gum sucrose at 0° to 4° C. shows identical staining patterns and intensity compared with a freshly processed portion of said tissue.

2. The process set forth in claim 1, including embedding said tissue in paraffin after said wash in xylene.

3. The process set forth in claim 1, wherein said formol sucrose solution is prepared by combining 2 grams of $NaH_2PO_4 \cdot H_2O$, 3.75 grams of sucrose, 50 milliliters of formaldehyde, 0.05 $NaN_3$ and 450 ml. of deionized water.

4. The process set forth in claim 1, wherein said gum sucrose solution is prepared by combining and mixing 150 grams of sucrose, 5 grams of gum Acacia, and 0.05 grams $NaN_3$; and adding deionized water to a volume of 500 milliliters.

5. The process set forth in claim 1, wherein said acetone-water solution is prepared by mixing 50% acetone and 50% water, by volume.

6. The process set forth in claim 2, wherein said tissue is embedded in paraffin by repeatedly immersing in warm paraffin.

7. The process set forth in claim 6, wherein said paraffin is at a temperature between about 58° to 61° C.

8. The process set forth in claim 1, including storing said tissue in gum sucrose at a temperature between 0° to 4° C. after said wash in xylene.

9. The process set forth in claim 1, including storing said tissue in paraffin after said wash in xylene.

10. The process set forth in claim 1, wherein said phosphate-buffered saline solution is at a pH of about 7.3.

11. The process set forth in claim 1, wherein said acetone-water solution and said acetone are at temperatures between about 0° to 4° C., and said tissue is washed in each for at least about one-half hour.

12. A tissue preserved by the process of claim 1.

13. A tissue preserved by the process of claim 6.

14. A tissue preserved by the process of claim 2.

15. A tissue preserved by the process of claim 7.

16. A tissue preserved by the process of claim 3.

17. A tissue preserved by the process of claim 4.

18. A tissue preserved by the process of claim 5.

* * * * *